(12) United States Patent
Pijuan Galito et al.

(10) Patent No.: US 10,011,816 B2
(45) Date of Patent: Jul. 3, 2018

(54) METHOD FOR CELL CULTURE

(71) Applicant: GE Healthcare BioSciences AB, Uppsala (SE)

(72) Inventors: Sara Pijuan Galito, Uppsala (SE); Christoffer Tamm, Uppsala (SE); Cecilia Anneren, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 15/289,076

(22) Filed: Oct. 7, 2016

(65) Prior Publication Data

US 2017/0022471 A1 Jan. 26, 2017

Related U.S. Application Data

(63) Continuation of application No. 15/190,065, filed on Jun. 22, 2016, which is a continuation-in-part of application No. 14/780,873, filed as application No. PCT/SE2014/050373 on Mar. 27, 2014.

(30) Foreign Application Priority Data

Mar. 28, 2013 (SE) ...................... 1350400

(51) Int. Cl.
| | |
|---|---|
| *C12N 5/02* | (2006.01) |
| *C12N 5/074* | (2010.01) |
| *C12N 5/00* | (2006.01) |
| *C12N 5/0735* | (2010.01) |

(52) U.S. Cl.
CPC ......... *C12N 5/0037* (2013.01); *C12N 5/0606* (2013.01); *C12N 5/0696* (2013.01); *C12N 2501/727* (2013.01); *C12N 2501/734* (2013.01); *C12N 2501/999* (2013.01); *C12N 2533/50* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 9,714,415 B2 | 7/2017 | Galito et al. | |
| 2007/0010008 A1 | 1/2007 | Tseng et al. | |
| 2007/0128719 A1 | 6/2007 | Tseng et al. | |
| 2007/0160594 A1 | 7/2007 | Filvaroff et al. | |
| 2012/0219737 A1* | 8/2012 | Sugino | C12N 5/0621 428/35.6 |
| 2016/0053225 A1* | 2/2016 | Pijuan Galito | C12N 5/0606 435/377 |
| 2016/0340646 A1* | 11/2016 | Pijuan Galito | C12N 5/0606 |
| 2017/0096642 A1 | 4/2017 | Pijuan Galito et al. | |

FOREIGN PATENT DOCUMENTS

| | | |
|---|---|---|
| EP | 2978839 A1 | 2/2016 |
| JP | 2005501513 A | 1/2005 |
| WO | 9640866 A1 | 12/1996 |
| WO | 2008002329 A2 | 1/2008 |
| WO | 2014/158089 A1 | 10/2014 |

OTHER PUBLICATIONS

Tamm et al., "Regulation of mouse embryonic stem cell self-renewal by a Yes-YAP-TEAD2 signaling pathway downstream of LIF", Journal of Cell Science, vol. No. 124, pp. 1136-1144, 2011.
Unofficial English Translation of Sweden Office Action issued in connection with corresponding SE Application No. 1350400-6 dated Sep. 20,2013.
Tamm et al., "A Comparative Study of Protocols for Mouse Embryonic Stem Cell Culturing", Comparison of Protocols for ES Cell Culturing, vol. No. 8, Issue No. 12, pp. 1-10, Dec. 10, 2013.
PCT Search Report and Written Opinion issued in connection with corresponding PCT Application No. PCT/SE2014/050373 dated May 23, 2014.
Wu et al. "Human Amniotic Epithelial Cells Express Specific Markers of Nerve Cells and Migrate Along the Nerve Fibers in the Corpus Callosum", Neural Regeneration Research, 2012, vol. 7, No. 1, 22 pages.
Petrey et al., "Hyaluronan, a Crucial Regulator of Inflammation", Frontiers in Immunology vol. 5, Article 101, Mar. 11, 2014, pp. 1-13.
Zhuo et al., "Inter-α-trypsin Inhibitor, a Covalent Protein-Glycosaminoglycan-Protein Complex",The Journal of Biological Chemistry, vol. 279, No. 37, 2004, pp. 38079-38082.
Evanko et al., "Hyaluronan-Dependent Pericellular Matrix", Adv Drug Deliv Rev.,vol. 59, No. 13, 2007, pp. 1351-1365.
Messina et al., "Isolation and Expansion of Adult Cardiac Stem Cells From Human and Murine Heart," Circulation Research, American Heart Association, Inc., vol. 95, No. 9, Oct. 29, 2004, pp. 911-921.
Zhang et al., "Constitutive Expression of Inter-inhibitor (IaI) Family Proteins and Tumor Necrosis Factor-simulated Gene-6 (TSG-6) by Human Amniotic Membrane Epithelial and Stromal Cells Supporting Formation of the Heavy Chain-Hyaluronan (HC-HA) Complex," Journal of Biological Chemistry, vol. 287, No. 15, Apr. 6, 2012, pp. 12433-12444.
West et al., "Angiogenesis Induced by Degradation Products of Hyaluronic Acid", Science, vol. No. 228, pp. 1324-1326, Mar. 25, 1985.
Enghild et al., "Analysis of lmter-a-trypsin Inhibitor and a Novel Trypsin Inhibitor, Pre-a-trypsin Inhibitor, from Human Plasma", The Journal of Biological Chemistry, vol. No. 264, Issue No. 27, pp. 15975-15981, Sep. 25, 1989.
Chen et al., "Identification of a Factor in Fetal Bovine Serum That Stabilizes the Cumulus Extracellular Matrix", The Journal of Biological Chemistry, vol. No. 267, Issue No. 17, pp. 12380-12386, Jun. 15, 1992.
Jiang et al., "Involvement of a Protein Distinct from Transcription Enhancer Factor-1 (TEF-1) in Mediating Human Chorionic Somatomammotropin Gene Enhancer Function through the GT-IIC Enhanson in Choriocarcinoma and COS Cells", The Journal of Biological Chemistry, vol. No. 270, Issue No. 23, pp. 13906-13915, Jun. 9, 1995.

(Continued)

*Primary Examiner* — Maria Marvich
(74) *Attorney, Agent, or Firm* — Wood IP LLC

(57) ABSTRACT

A method for stem or progenitor cell culture. More precisely, the invention relates to a method for cell culture using one or more IαI (inter-alpha trypsin inhibitor or inter-alpha inhibitor) protein(s) or part(s) thereof as a component in a cell culture media or a coating on a cell culture surface material. Furthermore the invention relates to a cell culture media and a cell culture coating/matrix provided with one or more IαI proteins(s) or part(s) thereof.

28 Claims, 9 Drawing Sheets

(56) References Cited

OTHER PUBLICATIONS

Trochon et al., "Evidence of Involvement of Cd44 in Endothelial Cell Proliferation, Migration and Angiogenesis In Vitro", International Journal of Cancer, vol. No. 66, pp. 664-668, 1996.

Wisniewski et al., "TNF/IL-1-Inducible Protein TSG-6 Potentiates Plasmin Inhibition by Inter-cw-Inhibitor and Exerts a Strong Anti-Inflammatory Effect In Vivo", The Journal of Immunology, vol. No. 156, pp. 1609-1615, 1996.

Blom et al., "Structural Characterization of Inter-a-inhibitor Evidence for an Extended Shape", The Journal of Biological Chemistry, vol. No. 274, Issue No. 1, pp. 298-304, Jan. 1, 1999.

Pienimaki et al., "Epidermal Growth Factor Activates Hyaluronan Synthase 2 in Epidermal Keratinocytes and Increases Pericellular and Intracellular Hyaluronan", The Journal of Biological Chemistry, vol. No. 276, Issue No. 23, pp. 20428-20435, Jun. 8, 2001.

Itano et al., "Abnormal accumulation of hyaluronan matrix diminishes contact inhibition of cell growth and promotes cell migration", Proceedings of the National Academy of Sciences, vol. No. 99, Issue No. 6, pp. 3609-3614, Mar. 19, 2002.

Toole et al., "Hyaluronan and Tumor Growth", American Journal of Pathology, vol. No. 161, Issue No. 3, pp. 745-747, Sep. 2002.

Baier et al., "Photocrosslinked Hyaluronic Acid Hydrogels: Natural, Biodegradable Tissue Engineering Scaffolds", Biotechnology and Bioengineering, vol. No. 82, Issue No. 5, pp. 579-589, Jun. 5, 2003.

Schoenfelder et al., "Expression of Hyaluronan Synthases and Corresponding Hyaluronan Receptors Is Differentially Regulated During Oocyte Maturation in Cattle", Biology of Reproduction, vol. No. 69, pp. 269-277, 2003.

Qi et al., "BMP4 supports self-renewal of embryonic stem cells by inhibiting mitogen-activated protein kinase pathways", PNAS, vol. No. 101, Issue No. 16, pp. 6027-6032, Apr. 20, 2004.

Josic et al., "Proteomic characterization of inter-alpha inhibitor proteins from human plasma", Proteomics, vol. No. 6, pp. 2874-2885, 2006.

Zhu et al., "The Role of the Hyaluronan Receptor CD44 in Mesenchymal Stem Cell Migration in the Extracellular Matrix", Stem Cells, vol. No. 24, pp. 928-935, 2006.

Watanabe et al., "A ROCK inhibitor permits survival of dissociated human embryonic stem cells", Nature Biotechnology, vol. No. 25, Issue No. 6, Jun. 2007.

Andang et al., "Optimized mouse ES cell culture system by suspension growth in a fully defined medium", Nature Protocols, vol. No. 3, Issue No. 6, pp. 1013-1017, 2008.

Moliner et al., "Mouse Embryonic Stem Cell-Derived Spheres with Distinct Neurogenic Potentials", Stem Cells and Development, vol. No. 17, pp. 233-243, 200.

Ying et al., "The ground state of embryonic stem cell self-renewal", Nature, vol. No. 453, pp. 519-523, May 22, 2008.

Block et al., "Improving post-transfer survival of bovine embryos produced in vitro, Actions of insulin-like growth factor-1, colony stimulating factor-2 and hyaluronan", Advances in Bovine Reproduction and Embryo Technology, Theriogenology, vol. No. 76, pp. 1602-1609, 2011.

Chen et al., "Chemically defined conditions for human iPSCSC derivation and culture", Nature Methods, vol. no. 8, Issue No. 5, pp. 424-431, May 2011.

Japan Notice of Preliminary Rejection for Japanese Patent Application No. 201480018671.9, dated Feb. 24, 2018, 6 pages. (English Translation).

Sara Pijuan-Galito et al., "Human Serum-Derived Protein Removes the Need for Coating in Defined Human Pluripoten Stem Cell Culture," Nature Communications, Article published Jul. 13, 2016, 12 pages.

Stavros Garantziotis et al., "Inter-a-Trypsin Inhibitor Attenuates Complement Activation and Complement-Induces Lung Injury," The Journal of Immunology, 2007, 179, pp. 4187-4192.

R.D. Geisert et al., "Expression of Inter-a-Trypsin Inhibitor Heavy Chains in Endometrium of Cyclic and Pregnant Gilts," 2003, Reproduction 126, pp. 621-627.

* cited by examiner

FIGURE 2

| IαI FAMILY PROTEINS | |
|---|---|
| Name | Combination of mature polypeptides |
| Bikunin | Free bikunin |
| IαI | HC1 + HC2 + bikunin |
| PαI | HC3 + bikunin |
| IαIH2,B | HC2 + Bikunin |
| IαIH1,2 | HC1 + HC2 (human, SHAP) |
| IαIH4P | Free H4P |
| Others | Intermediate and/or unknown species; IαIH1,B; IαIH4,B; p236 or IαIH2,3,B, HC5, etc. |

| Coating | No coating | Vitronectin | No coating | HC2 20 µg/ml |
|---|---|---|---|---|
| Media/Supplement | E8 | E8 | E8 + IαI 10µg/ml | E8 |
| Human iPS cell line K02C p54 |  |  |  |  |

K02C human iPS cell line
Passage 67

E8 Media + VN peptide coating
Passage 16

E8 Media + IαI 20 µg/ml
Passage 14

METHOD FOR CELL CULTURE

CROSS REFERENCE TO RELATED APPLICATIONS

This application is a continuation of U.S. application Ser. No. 15/190,065, filed on Jun. 22, 2016, which is a continuation in part of U.S. patent application Ser. No. 14/780,873 filed on Sep. 28, 2015 which is a filing under 35 U.S.C. 371 and claims priority to international patent application number PCT/SE2014/050373 filed on Mar. 27, 2014, which claims priority to patent application Ser. No. SE1350400-6 filed in Sweden on Mar. 28, 2013 in English.

TECHNICAL FIELD

The present disclosure relates to a method for cell culture. More precisely, the disclosure relates to a method for cell culture using one or more IαI (inter-alpha trypsin inhibitor or Inter-alpha inhibitor) protein(s) or part(s) thereof as a component in a cell culture media or a coating on a cell culture surface material. Furthermore the disclosure relates to a cell culture media and a cell culture coating/matrix provided with one or more IαI proteins(s) or part(s) thereof.

BACKGROUND

Pluripotent stem (PS) cells e.g. embryonic stem (ES) cells and induced pluripotent stem (iPS) cells have the ability to maintain pluripotency during long-term culture and yet induce differentiation into multiple lineages and therefore potentially offer novel cell sources for e.g. basic research, toxicological screening, in vitro modeling of genetic disorders or therapeutic cell replacement. There are still many obstacles to overcome until these endpoints can be fully realized. For instance it will be necessary to find culture conditions that support safe, simple and robust derivation, growth, maintenance and large-scale expansion, while maintaining self-renewal, of these difficult to culture cells. Especially important is the need for methods for maintenance of human PS cells in vitro. These methods have to be good enough to maintain the population of cells without inducing mutagenesis, high levels of differentiation or loss of pluripotency.

Mouse ES cells are extensively used in basic research to e.g. study normal and pathological development and function and the knowledge obtained using these cells is often transferred to human systems. Most mouse ES (mES) cell lines used today are grown on pre-plated mitotically inactivated mouse embryonic fibroblast (MEF) feeder cells in media supplemented with selected batches of fetal bovine serum (FBS) and Leukemia inhibitory factor (LIF). The feeder cells provide a matrix that support mES cell attachment and secrete various growth factors that enhance the survival and propagation of mES cell growth whereas FBS provides hormones and essential nutrients, as well as altering the physiological/physiochemical properties of the medium. LIF drastically improves the derivation and maintenance of the pluripotency of mES cells. Some mES cell lines have been derived and adapted to grow feeder-free on 0.1% Gelatin coating (heterogeneous mixture of water-soluble proteins of high average molecular weight present in collagen and extracted from bovine skin) in serum and LIF containing media. Both these cell culture protocols have the shortcoming that many of their components (i.e. FBS, bovine serum albumin or BSA, gelatin) are not defined and are animal-derived. FBS, for instance, contains various growth factors and other undefined components that promote ES cell growth, but it has also been suggested to contain potential differentiation factors that can affect mES cell plating efficiency, growth and differentiation. Therefore FBS batches need to be pre-screened and ES-qualified to ensure that the net-effect of serum factors that sustain mES cell maintenance and growth outweighs the effects of differentiation-inducing factors. Feeders in their turn secrete a plethora of factors impossible to control and are a possible source of pathogenic contamination.

To improve control of what factors ES cells are actually subjected to, and to avoid interference from undesired factors, several newer and more defined protocols have been established. In 2003 it was shown that BMP4 could be efficiently used in combination with LIF for mES derivation and maintenance in serum- and feeder-free cultures (Qi, Li et al. 2004). In 2004, a chemically defined (the exact formulation is not described) synthetic knockout serum replacement (KOSR) was developed to replace serum. However, the KOSR cannot alone support mES single-cell culture in the absence of feeders. In 2008, it was shown that mES could be maintained in the absence of serum and feeder cells as free-floating spheres in a N2 supplemented medium with LIF and bFGF (basic fibroblast growth factor), herein named ESN2 medium (Andang, Moliner et al. 2008, Moliner, Enfors et al. 2008).

Recently, another defined media supplemented with two inhibitors, the mitogen-activated protein kinase (MAPK)/extracellular-signal-regulated kinase (ERK) kinase (MEK) inhibitor PD0325901 and the glycogen synthase kinase 3 (GSK3) inhibitor CHIR99021, added to a B27 and N2 supplemented medium (herein named 2i medium) was shown to maintain mES cell self-renewal without the addition of exogenous factors (Ying, Wray et al. 2008). Mouse ES cells cultured in 2i medium still respond to LIF, which enhances cloning efficiency and proliferation rates. A drawback with this culture protocol is that, in the absence of serum, the cells do not adhere to the tissue culture plate but instead grow as free-floating spheres (Tamm, Pijuan Galito et al. 2013); moreover, the growth rate of the mES cells is decreased.

Human PS (hPS) cells and their differentiated cells are most commonly cultured in the presence of surfaces or media containing animal-derived components, such as feeder layers (both mouse-derived, typically MEFs, and human-derived, typically human foreskin fibroblasts or HFFs), Matrigel® (soluble basement membrane extract of the Engelbreth-Holm-Swarm EHS tumor), knock out serum replacement (KOSR) and/or derivatives like BSA. These animal-derived reagents added to the culture environment expose the cells to potentially harmful viruses or other infectious agents, which could be transferred to patients or compromise general culture and maintenance of the hPS cells. In addition, such biological products are vulnerable to batch variations, immune responses and limited shelf-life, and the exposure of the cells to molecules from other species also creates changes that could create an immune response in the recipient, if the cells were to be used in cell therapy.

To date, several completely recombinant, xeno-free systems employing a chemically defined medium and a synthetic or defined surface have been described. The most recent success in human PS cells culturing was published in Nature methods in 2011 describing a chemically reduced and completely defined media, named E8 only containing 8 different chemical components, that could support hiPS cell derivation and further successful culture on Matrigel® or a vitronectin-based surface (Chen, Gulbranson et al. 2011).

Even so, different cell lines and different laboratories obtain different results when using defined media, and the most widely used protocols are still the combination of Matrigel® and mTESR1® (which contains BSA, purified from FBS) for hPS cells; and Gelatin coating and media supplemented with FBS for mES cells. Moreover, hPS cells cannot be split as single cells if not in the presence of the ROCK-inhibitor molecule (i.e. Y-27632) (Watanabe, Ueno et al. 2007), and for routine passaging need to be split in clumps with a gentle dissociation technique, proving the crucial role of the extracellular environment for pluripotent stem cells.

There is still an urgent need to understand all the different components necessary for the growth and maintenance of undifferentiated, non-mutated, pluripotent stem cells. It is important to get the right combination of extracellular matrix (ECM) and media factors, especially for the human PS cell lines, otherwise the cells show low attachment, survival and proliferation rates, as well as high levels of differentiation.

For the sake of cell survival and proliferation rate, current protocols for cell culture still use FBS or derivatives such as BSA in the cell culture media and, thus, there is still need of an improved serum free protocol that does not compromise the cells, the culture conditions or the pluripotency.

SUMMARY

In the present disclosure a factor that promotes cell adhesion and long-term cell culture viability has been discovered. More precisely, the present disclosure provides the novel use of Inter-alpha trypsin inhibitor (IαI) family proteins(s) or part(s) thereof, in particular HC2 (heavy chain 2), as a surface coating and/or media additive for cell adhesion and long-term culture, maintenance and growth of pluripotent stem cells for at least five passages, in the presence of partially or completely chemically defined media, without inducing noticeable differentiation or karyotype abnormalities. In some embodiments, the cell adhesion and long-term culture, maintenance and growth of pluripotent stem cells are maintained for at least 20 passages.

Thus, in a first aspect the present disclosure provides a method for culturing stem or progenitor cells, comprising addition of one or more protein(s) from the IαI (inter alpha trypsin inhibitor) protein family or part(s) thereof to a serum-free culture medium to promote adhesion and renewal of said cells. In an embodiment, the cells are stem cells. The addition of IαI according to an embodiment of the disclosure promotes self-renewal, attachment, survival and, in the case of PS cells, also pluripotency. The IαI proteins(s) or part(s) thereof are isolated from serum, produced as a recombinant protein, synthesized chemically, or produced with a combination of these methods.

In an embodiment, the cells are adherent cells and in another embodiment the cells are PS (pluripotent stem) cells, and may be ES (embryonic stem) cells or iPS (induced pluripotent stem) cells. In one embodiment of the disclosure the cells are of human origin.

In an embodiment, the IαI protein or part thereof is selected from IαI (IαIHC1, IαIHC2 and bikunin) or IαIH2, B. The heavy chains of the IαI proteins may be used, such as heavy chain 2 (HC2) from IαI.

In case of PS cells in an embodiment of the present disclosure, the cell culture is serum free.

In one embodiment the IαI proteins(s) or part(s) thereof are coated onto a cell culture surface, such as plastic, carriers, scaffolds, matrices or meshes, as a coating agent.

In another embodiment the IαI proteins(s) or part(s) thereof are added to a serum-free cell culture medium.

The concentration of the IαI proteins(s) or part(s) thereof is 0.1 μg/mL-200 μg/mL, for example 2-100 μg/mL, or 10-50 μg/mL in culture medium or coating solution.

The method according to an embodiment of the present disclosure is suitable for cell culture during at least twenty passages without inducing differentiation or mutation of the cells. Following cell culture, the PS cells may be prepared/provided for, for example: cell therapy, drug screening and toxicity assays.

In a second aspect, the present disclosure provides a cell culture media comprising IαI protein(s) or part(s) thereof in a concentration of 0.1 μg/mL-200 μg/mL, for example 2-100 μg/mL or 10-50 μg/mL. In an embodiment, the media is a serum free culture media.

In a third aspect, the present disclosure provides a cell culture surface comprising a coating comprising IαI protein(s) or part(s) thereof in the above concentrations. The coating may take place overnight at 4° C., or 1-2 h at RT or 37° C., at a range of coating concentrations of 0.1 μg/mL-200 μg/mL, for example 2-100 μg/mL or 10-50 μg/mL.

In a fourth aspect, the present disclosure relates to use of IαI proteins, more particularly IαI or H2 for cell adhesion and renewal.

In a fifth aspect, the present disclosure relates to a method for culturing stem or progenitor cells, comprising growing said cells on an uncoated surface in a cell culture medium comprising one or more proteins from an inter alpha trypsin inhibitor (IαI) protein family or parts thereof to promote adhesion of said cells to said uncoated surface as well as self renewal of said cells. A method according to claim 1, wherein the one or more IαI proteins or parts thereof are un-complexed proteins isolated from serum or a serum fraction, produced as a recombinant protein, synthesized chemically, or a combination thereof. For example, uncoated surface is an uncoated or naked culture plastic. In one embodiment, the stem cells are pluripotent stem (PS) cells. In one embodiment, the cells are of human origin. The one or more IαI proteins or parts thereof for example can be selected from IαI or IαIH2,B (H2). In some embodiments, the cell culture is whole serum free and serum component free.

In one embodiment, the one or more IαI proteins or parts thereof are added to a cell culture surface as a coating agent, and wherein said culture is devoid of said proteins or parts thereof. The concentration of the one or more IαI proteins or parts thereof can be 0.1 μg/mL-200 μg/mL for example 2-100 μg/mL or 10-50 μg/mL in the cell culture medium. In one embodiment, heavy chains of the one or more IαI proteins are used, for example heavy chain 2 (H2) from the IαI protein is used. In one embodiment, the cell culture goes through at least five passages without inducing differentiation or mutation of the cells. In another embodiment, the cell culture goes through at least ten passages without inducing differentiation or mutation of the cells. In a further embodiment, the cell culture goes through at least twenty passages without inducing differentiation or mutation of the cells.

In a sixth aspect, the present disclosure relates to a cell culture media comprising one or more inter alpha trypsin inhibitor (IαI) proteins or parts thereof in a concentration of 0.1 μg/mL-100 μg/mL for example 2-40 μg/mL or 5-10 μg/mL.

In a seventh aspect, the present disclosure relates to a cell culture surface comprising a coating comprising one or more inter alpha trypsin inhibitor (IαI) proteins or parts thereof in a concentration of 0.1 μg/mL-200 μg/mL, for example 1-100 μg/mL or 10-50 μg/mL.

The inter alpha trypsin inhibitor (IαI) protein can be used for cell adhesion and self-renewal of pluripotent stem (PS) cells on an uncoated cell culture surface to support single cell survival both with and without Rho-associated kinase inhibitor (ROCKi). In one embodiment, the PS cells are primed or naïve embryonic stem (ES) cells or induced pluripotent stem (iPS) cells. In one embodiment, the IαI proteins or parts used is heavy chain 2 (H2). In one embodiment, the cells are subjected to clonal growth.

In an eighth aspect, the present disclosure relates to cultured undifferentiated or unmutated stem or progenitor cells. The cells are produced by culturing stem or progenitor cells using the methods disclosed herein. In one embodiment, the cells are cultured on an uncoated surface in a cell culture medium comprising one or more proteins from an inter alpha trypsin inhibitor (IαI) protein family or parts thereof. In one embodiment, the cultured cells went through at least five passages. In one embodiment, the cultured cells are human pluripotent stem cells.

One or more of the various Inter-alpha trypsin inhibitor proteins(s) or part(s) will provide advantages over prior coating materials for culture of pluripotent stem cells, particularly undifferentiated, non-transformed, pluripotent stem cell lines. For example, the purification of Inter-alpha trypsin inhibitor proteins or parts thereof from human serum provides an animal-component free matrix and the usage of the side fraction from the commercial production of factor IX makes the process relatively simple and economic. However, the subparts of IαI could also be recombinantly expressed or synthesized chemically to make them completely defined.

The ability to culture undifferentiated cells on a chemically defined surface or medium eliminates extra contamination components from animal serum components typical from complex medias. In addition, the batch to batch variation will be also reduced in comparison to serum and serum-derived additives such as serum (e.g., FBS), KOSR and BSA, as it would not rely on the proportional concentrations of different components. These and other advantages will be understood from the following description when read in conjunction with the enclosed figures.

BRIEF DESCRIPTION OF THE DRAWINGS

FIG. 2 shows an overview of IαI family of proteins.

DETAILED DESCRIPTION

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The present disclosure may be understood more readily by reference to the following detailed description of embodiments and to the Figures and their previous and following description.

Figure 1:
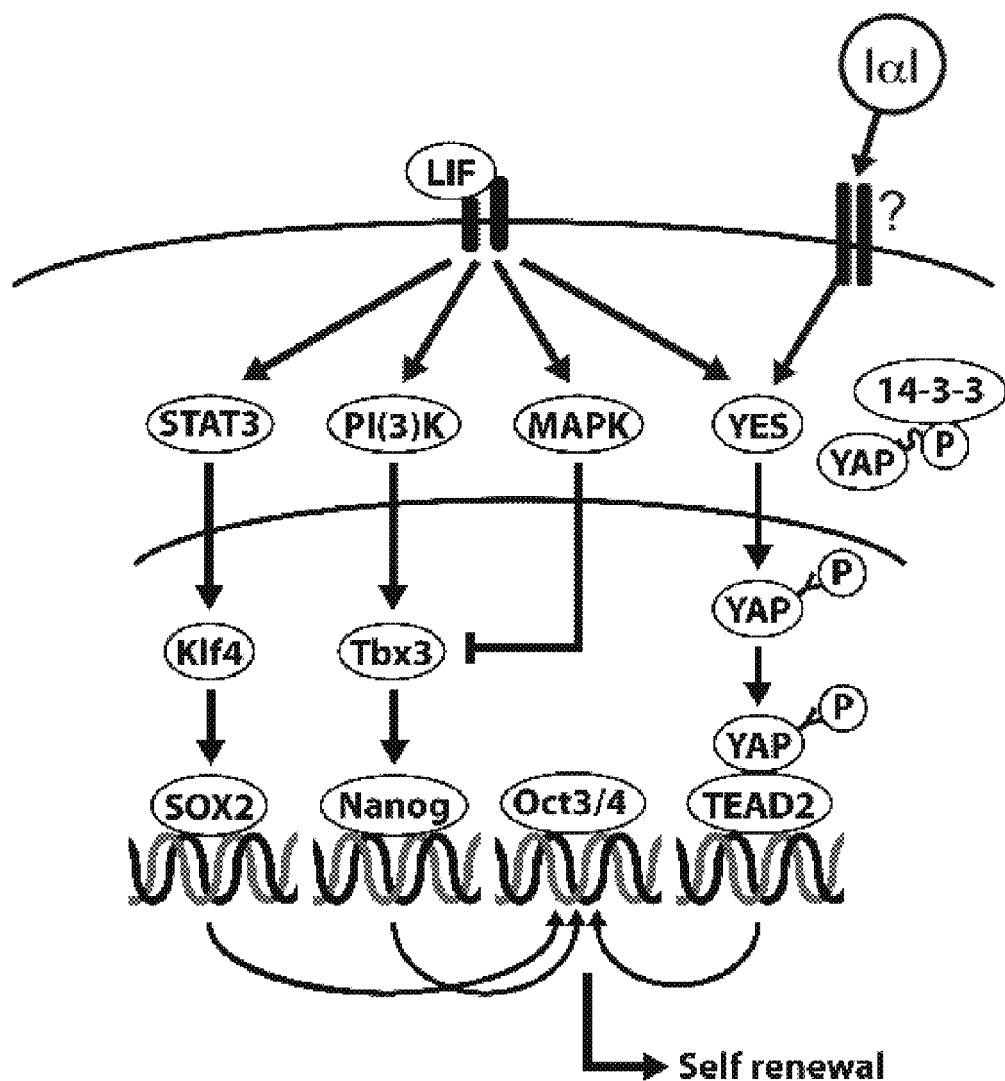
FIG. 1 is a schematic view of some of the self-renewal pathways in mES cells and shows the incorporation of IαI protein in TEAD2-Yes-YAP pathway.

It has been previously described that a novel kinase pathway is involved in the maintenance of self-renewal and pluripotency by mouse embryonic stem (mES) cells (Tamm, Bower et al. 2011). Briefly, a new path downstream of the LIF receptor was found with the activation of the Src kinase Yes, which in turn activated cytoplasmic Yes-associated protein (YAP) which would enter the nucleus and form a transcription complex with TEAD2, activating the transcription of other well described self-renewal and pluripotency factors such as Oct3/4 and Nanog as shown in FIG. 1.

Applicants have found that FBS can also activate TEAD2-dependent transcriptional activity. Through a set of fractionation techniques it was managed to identify one component in serum that activates the TEAD2-dependent transcription. The isolated protein was identified as a component of the Inter-alpha trypsin inhibitor (IαI) family: ITIH2 or IαI heavy chain 2 (HC2).

The IαI protein family is a complex group of protein-glycosaminoglycan-protein (PGP) complexes that occur constitutively at quite high concentrations in serum (0.6-1.2 mg/mL in humans) (Josic, Brown et al. 2006), as a results of alternate combinations of five kinds of heavy chains: HC1, HC2, HC3, HC4 and HC5 (although this last two have not been found to form complexes and have been only found in serum alone as peptides) and the kunitz-domain protease inhibitor Bikunin (Bk) linked together by a Chondroitin sulphate (CS) chain. The two most common members of the IαI protein family are IαI (HC1, HC2 and Bk) and Pre-α-inhibitor (PαI, HC3 and Bk); although IαIH2 (HC2, Bk), IαIH4P (only HC4) and Bk alone can also be found in plasma (FIG. 2).

The IαI proteins are mainly produced by the liver; the pro-peptides are processed and assembled in the Golgi and then secreted into the blood stream. The IαI protein complexes are still mostly inactive until they reach their target tissue and are cleaved by the tumor-necrosis factor gene-associated protein 6 (TSG-6). TSG-6 cleaves the HC covalent bond with the chondroitin sulphate chain and forms a transient covalent bond with the HC to transfer it finally to hyaluronan (HA), a common part of the extra-cellular matrix. The bikunin domain increases in proteolytic activity in conjunction with TSG-6 (Wisniewski, Hua et al. 1996), and is solely responsible the protease inhibitory activity of IαI against trypsin, chymotrypsin, plasmin, cathepsin G, acrosin, and leukocyte elastase. Hyaluronan is a long, linear, non-sulphated glycosaminoglycan (GAG) made of the repeating disaccharide: (1-β-4)D-glucuronic acid and (1-β-3)N-acetyl-D-glucosamine. Hyaluronan has also been described as an important element in embryonic development (Schoenfelder and Einspanier 2003), tissue organization, (Trochon, Mabilat et al. 1996, Itano, Atsumi et al. 2002), wound healing (Pienimaki, Rilla et al. 2001, Baier Leach, Bivens et al. 2003), angiogenesis (West, Hampson et al. 1985), tumorigenesis (Toole and Hascall 2002), and possibly even in the biomechanical properties of tissues. In addition, it is well known that HA associates with cell-surface receptors and may help regulate cell motility and adhesion (Zhu, Mitsuhashi et al. 2006, Block, Hansen et al. 2011). The IαI-HCs have been the only proteins clearly demonstrated to bind covalently to HA. By binding the HA fibers in the tissues, the HCs can modify the niche of the cells and therefore play a role in e.g. adhesion, inflammation and ECM formation. Some studies suggest that IαI proteins not only have an important role in the control of inflammation and stabilization of the extracellular matrix, but could also induce the production and secretion of a HA-rich extracellular matrix when added to the cells.

Figure 4:
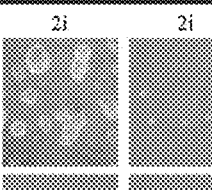
FIG. 4 shows attachment assay bright-field images of mES E14 cells grown 2i media on different coatings and/or with different media supplements.
Figure 6:
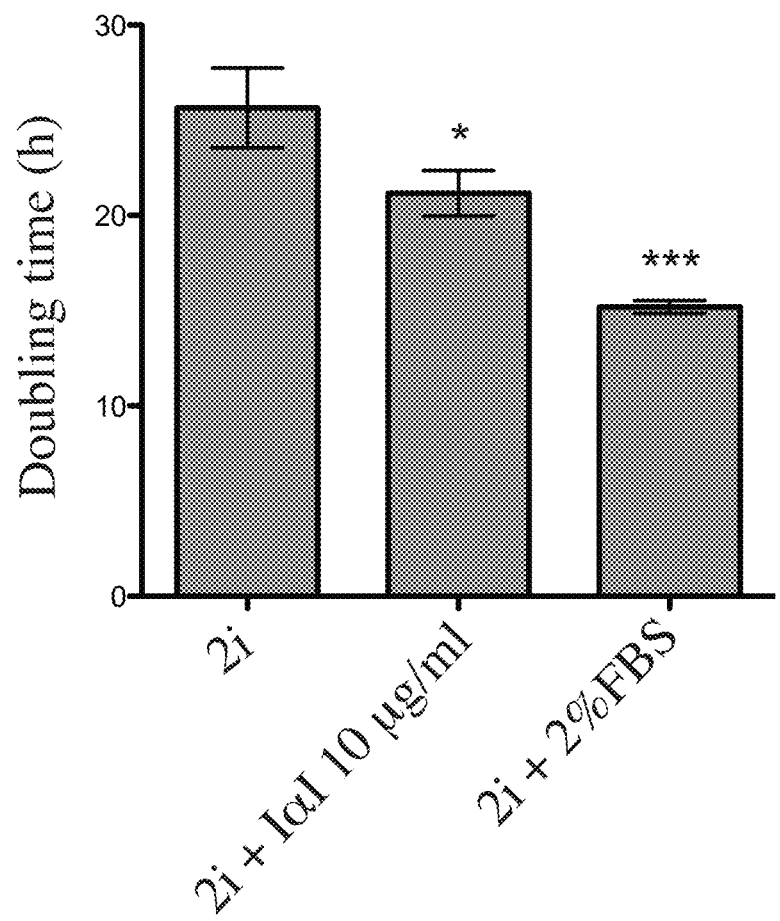
FIG. 6 shows the doublings times for mES cell line E14 grown for 3 passages in 2i media, 2i media supplemented with 2% FBS and 2i supplemented with IαI 10 μg/mL.

According to the present disclosure it has been found that II is important for PS cell culturing. When using the semi-defined media 2i, and the totally defined suspension media ESN2 with LIF and FGFb, mES cells grow in floating spheres and at a slower rate than in serum-containing conditions. Moreover, when the conventional coating surfaces gelatin, fibronectin and collagen were used, mouse ES cells in 2i or ESN2 media did not attach and continued growing as free floating spheres as shown in FIG. 4. The addition of 2% FBS made the cells adhere to the plastic surface in nice tight colonies and accelerates the doubling time. In some embodiments, the addition of the corresponding for example 10 µg/mL or lower amounts of IαI also achieves adhesion of the mES colonies to the plastic surface in the serum-free 2i media, increasing the proliferation rate compared to 2i medium alone as shown in FIGS. 4 and 6.

Four human PS cell lines were also tested for attachment when using a completely recombinant, serum-free media TeSR™-E8™. After one passage of E8 adaptation done step-wise from mTeSR™1 to TeSR™-E8™ (StemCell Technologies) the cells were seeded using different conditions. FIG. 4 shows attachment data on the human iPS cell line K02C. The negative control shows no attachment on non-coated plates when no supplementation is added to the commercial TeSR™-E8™ media, while they sit down on plastic dishes coated using a vitronectin peptide (Vitronectin FX™, StemCell Technologies). The human iPS cell line K02C also sits down on plastic dishes coated using 20 µg/mL IαI-HC2. Moreover, the supplementation of the media with a concentration ranging from 10 to 50 µg/mL of human, purified, complete molecule IαI also induced attachment of the human iPS cells on non-coated plastic dishes as shown in FIG. 4. The human ES cell lines H181 and H207 (kindly provided by Dr. Outti Houvatta) and HUES1 (kindly provided by Dr. Douglas A. Melton) showed the same attachment behavior under the same conditions, and maintained pluripotency as well as colony morphology when cultured for over 5 passages in TeSR™-E8™ medium supplemented with 20 µg/mL IαI.

According to an embodiment of the present disclosure, IαI may form part of the ECM of PS cells and modify the properties or their niche, inducing extracellular matrix formation and/or remodeling. Also IαI may be added to defined cultures in order to promote attachment and provide a good environment for the cell survival and proliferation in vitro. IαI binds to the cells, modifying the signaling from their environment and improving survival after splitting and maintenance of self-renewal and pluripotency.

In some embodiments, the IαI disclosed herein can be used for single cell culturing. Specifically, routine culture usually involves passage in small aggregates or clumps to avoid a loss of viability associated with dissociation (anoikis). The addition of ROCKi (Y-27632) to the hPS cell medium increases survival after single-cell passaging, but it is costly, particularly at scale.

Figure 9:
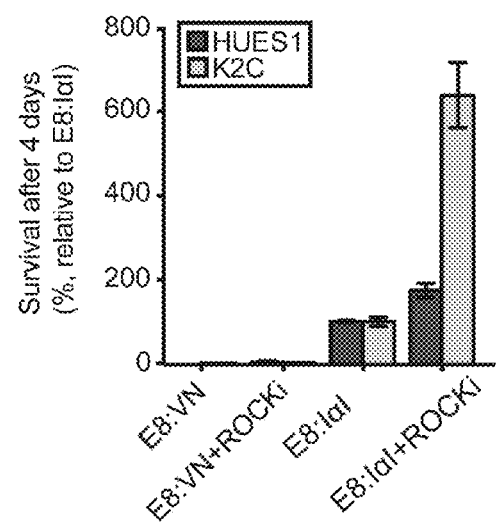
FIG. 9 shows quantification of HUES1 and K2C cell survival and growth, using crystal violet staining, after 4 days in culture on VN-FX coat or with IαI supplementation after single-cell passaging with or without addition of 10 μM ROCKi after seeding, no ROCKi pre-treatment.
Figure 10:
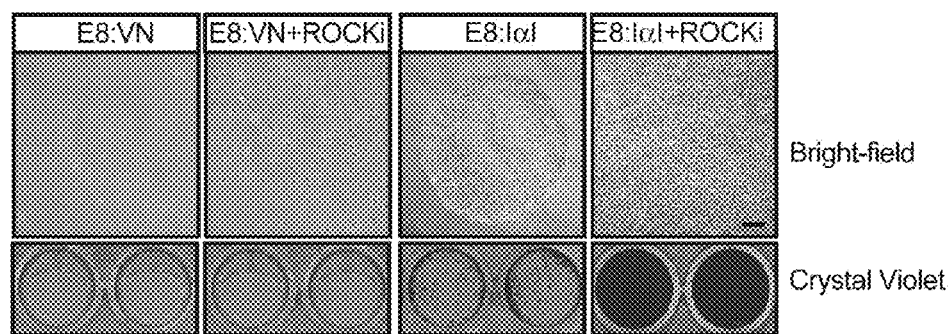
FIG. 10 shows representative images for HUES1 cell line, bright-field pictures on the top and overview of crystal violet on the bottom.

When sub-culturing in small aggregates, 50 µg mL$^{-1}$ of IαI supplementation at the seeding step support similar viability as VN-FX coating. However, when performing single-cell splitting, almost no cells had survived after 4 days on VN-FX coating even with the addition of 10 µM ROCKi to the culture during the first 24 hours after seeding. In contrast, under these conditions, IαI supplementation supported very high cell survival, with cells reaching a monolayer after 4 days. Further analysis showed that IαI was also able to support survival and colony formation of dissociated single cells in the absence of ROCKi, although the survival rate was lower than with ROCKi as shown in FIGS. 9 and 10.

The cloning success rate for six different hPS cell lines (K2C, HUES1, H207, H181, NCL1 and K8F) cultured in E8:IαI or E8:VN has also been assessed. High cloning rates of up to 18% were achieved with E8:IαI, and the cloning efficiency was consistently higher using the E8:IαI protocol as compared to E8:VN protocol in all 5 hPS cell lines tested, despite using a 5 hour pre-treatment with ROCKi.

EXAMPLES

Example 1

Serum Fractionation and Identification of the Active Fractions in TEAD2-Dependent Transcription Activation Fetal Bovine Serum (FBS) was first treated with a mild acetonitrile (ACN) precipitation to separate smaller proteins from its carriers as previously described (Lei et al, 2008). Briefly, the FBS was diluted with the addition of 30% V/V of ddH$_2$O and 20% V/V of acetonitrile (ACN) and warmed to 40° C. for 15 min. The mixture was then centrifuged at 14,000×g for 10 min to precipitate any insoluble material. The supernatant was diluted in binding buffer for a modified Blue Sepharose Chromatography purification, as described previously (Arakawa et al, 2007). Briefly, 4 mL of diluted FBS was further diluted with the addition of 4 mL of a Saturated Ammonium Sulphate solution (SAS) and 24 mL of Binding buffer (20 mM Phosphate Buffer, 2M Ammonium sulphate, pH 7) before adding it to an equilibrated Blue Sepharose column (GE Healthcare). The column was subsequently washed with 20 mM Phosphate buffer pH 7 to remove all the bound Bovine Serum Albumin (BSA) and further eluted; first with 20 mM Phosphate buffer with 2M NaCl pH 7 and then with 20 mM Phosphate buffer 1M Arginine (Arg) pH 7.

The eluted fractions, Elution 1 and Elution 2, were concentrated and dialyzed against PBS using a Vivaspin 6 column (GE Healthcare) and then added to E14 mES cells in serum-free media and TEAD2-dependent transcription activity was assessed using a luciferase assay. E14 mES cell lines were seeded into 24 well plates in serum-containing media and Gelatin-coated plates and grown overnight until 70-80% confluence. The cells were then transfected using Lipofectamine™ 2000 (Life-Technologies) according to the manufacturer's recommendations, in OPTI-MEM serum-free media (Life Technologies) for 4 hours at 37° C. 5% $CO_2$ after which serum-free GMEM-based media was added to stop the transfection. The cells were transfected with pCS GT-IIC-luciferase (GTIIC) (Jiang and Eberhardt 1995) and the pCMV β-gal reference plasmid containing a bacterial β-galactosidase gene. After being serum-starved for 24 hours the cells were exposed to the different eluted fractions diluted into serum-free media and the TEAD2-dependent transcriptional activity was measured using a Luciferase assay. The cells were lysed and assayed for luciferase and β-galactosidase activities in a microplate luminometer and photometer reader (Wallac VICTOR 1420 Multilabel Counter: Perkin Elmer).

The first elution sample (2M NaCl) was found to have the most TEAD2-dependent transcription activation effect (FIG. 3A) and was further fractionated using with a conventional Heparin Chromatography (Pharmacia AB, now GE Healthcare). Briefly, the eluted fraction was concentrated and dialyzed against the Heparin Chromatography binding buffer 50 mM Tris-HCl pH 8 using a Vivaspin column 20 (GE Healthcare) and loaded on to an equilibrated column. The elution was made step-wise with 6 fractions of 1 mL volume with 0.05-0.1-0.2-0.5-1-2 M NaCl. The fractions were again dialyzed and concentrated using Vivaspin 6 columns into a cell-appropriate buffer and tested for TEAD2-dependent transcription as described above. The different eluted samples were analyzed using SDS-PAGE 10% acrylamide gel and Comassie Blue staining. The TEAD2-dependent transcription effect was compared to the protein patterns of the different fractions and two bands were identified as possible TEAD2-transcription activating molecules. The gel was sent for MS-MALDI-TOFF analysis (Åke Engstrom, IMBIM) and the bands were identified as 1) inter-alpha globulin inhibitor H2 polypeptide [*Bos taurus*] and 2) alpha-2-macroglobulin [*Bos taurus*].

Figure 3:
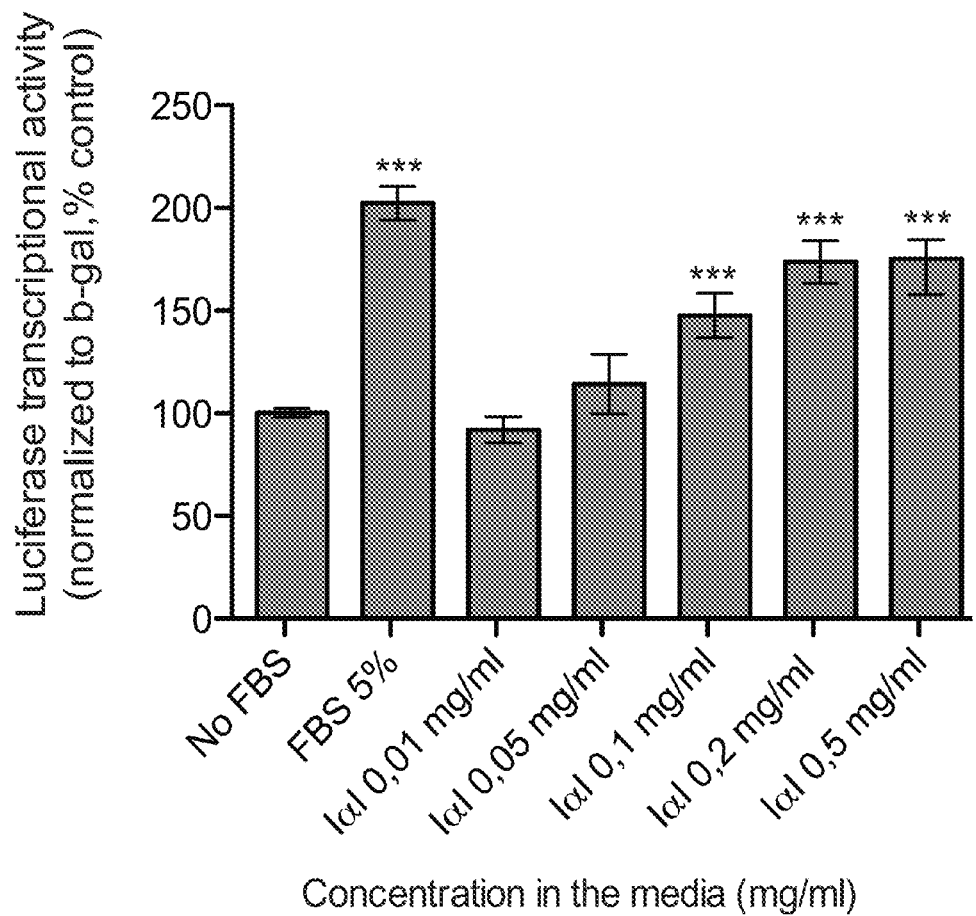
FIG. 3 shows a dose-response analysis of the effect of IαI on TEAD2-dependent transcription activity in mES cells.

Purified human IαI was tested on the cells as described above and a dose-respose test was performed. IαI exposure on the cells not only had a TEAD2-transcriptional activation effect but this effect also followed a dose-response trend reaching similar amounts than 5% FBS as shown in FIG. 3. Results are presented as the mean percentage of the control and SEM bars for at least three independent experiments made in triplicate and normalized to % of the control were the control is 100% for the serum-starved cells. Statistical analysis was done by One-way ANOVA with Dunnett's post test using GraphPad Prism version 5.00d for Mac (GraphPad Software, San Diego Calif. USA) where * represents $p<0.05$,  represents $p<0.001$ and * $p<0.001$.

Example 2

Assessment of Attachment of mES Cells in 2i Media on Different Conventional Surface Coating Proteins for Embryonic Stem Cells and Media Additives FBS or IαI Purification of Human IαI The isolation of IαI and the heavy chains HC1 and HC2 was made as described before (Blom, Morgelin et al. 1999). Briefly, a side fraction from the commercial production of factor IX was dialyzed against Phosphate-buffered saline (PBS) and centrifuged for the removal of insoluble protein aggregates. This material was then filtered and subjected to gel filtration on a HiPrep 26/60 Sephacryl S-400 HR, which yielded more than 95% pure IαI. For the release of the heavy chains, 2M NaOH was added to a solution of IαI of 1 mg/mL in PBS to give a final concentration of 0.05M NaOH (Enghild, Thogersen et al. 1989). After 15 min at room temperature, Tris-HCl pH 8.0 was added to yield a final concentration of 0.25M. The mixture was incubated for 1 hour at 37° C. The sample was then dialyzed against 20 mM sodium phosphate pH 7.6 overnight at 4° C., and applied to an anion exchange gel (MonoQ 5/50 GL; GE Healthcare) equilibrated with the same buffer. The proteins were eluted at a linear flow rate of 0.5 mL/min with 100 mL of a gradient from 0 to 0.7M NaCl in 20 mM sodium phosphate, pH 7.6 (Balduyck, Piva et al. 1993). The fractions were analyzed in 8% acrylamide SDS-PAGE gels followed by staining with Coomassie Brilliant Blue. Unless specified otherwise, protein concentrations were determined by UV measurements. The absorbance coefficients for the protein moieties of IαI, HC1 and HC2 were obtained from a former publication (Blom, Morgelin et al. 1999). The corresponding values for the whole proteins are 0.60, 0.47, and 0.72 $mg^{-1}$ mL $cm^{-1}$, for IαI, HC1 and HC2, respectively. The protein solutions were concentrated and dialyzed against PBS in Vivaspin 20 columns (GE Healthcare Bio-Sciences AB) and stored at −20° C. until they were used for experiments.

Addition of 2% FBS or 10 μg/mL IαI Increases Doubling Time of mES Cells in 2i Media The E14 mES cell line was maintained in continuous culture in 10% FBS and KOSR at 50/50 concentration in a GMEM-based media (Sigma) supplemented with Penicillin, Streptomycin, Glutamate, Pyruvate (all from Life technologies), β-Mercaptoethanol (Sigma) and LIF (Millipore), on 0.1% Gelatin (Sigma) coated cell culture dishes (Corning); as previously described (Smith, 1991). The cells were passaged under serum-free conditions using TrypLE™ (Life Technologies) into 2i Media (Ying, 2008 Nature), a N2B27 formulation with LIF, PD0325901 and CHIR99021 inhibitors (Selleckchem). After two passages all the cells were growing in floating spheres. The spheres were again passaged in serum-free conditions using TryPLE™ and then plated in 2i media, 2i media with 2% FBS and 2i media supplemented with 10 μg/mL of IαI. The cells were grown for 3 passages and counted in every passage to assess the proliferation rate. The supplemented media showed a higher proliferation rate than the cells grown in floating spheres with 2i media. The FBS supplemented media had the shortest doubling time with a mean of 15.19 hours. The IαI supplemented media had a longer doubling time of 21.16 hours but still shorter than the 25.64 hours of the floating spheres grown in 2i media as shown in FIG. 6. Statistical analysis further confirmed the significant difference in growth rates of the different formulations.

Assessment of Attachment of mES Cells in 2i Media on Different Conventional Surface Coating Proteins for Embryonic Stem Cells and Media Additives FBS or IαI The different coating proteins were diluted in PBS to final concentrations of 10 µg/mL Vitronectin, 10 µg/mL Fibronectin, 10 ug/mL Collagen I, 2% FBS, 25 µg/mL II and 50 µg/mL HC2. 12 well plate wells were coated with the different solutions for 2 hours at 37° C. 5% $CO_2$. The wells were washed with PBS, 3 times for the Vitronectin, Fibronectin, Collagen I and FBS, and washed once for IαI and HC2. The same number of E14 mES cells were seeded into the different coated wells after serum-free splitting in 2i media. After 48 hours the media was transferred to new wells and fresh media was added to the old well, pictures were taken of the remaining attached cells in the well (upper panel) and the floating cell spheres transferred with the supernatant (lower panel) to assess attachment as shown in FIG. 4. Similarly, E14 mES cells were passaged from 2i media in serum-free conditions using TryPLE™ and transferred to 2i media with or without 2% FBS, 5 µg/mL IαI, 10 µg/mL IαI or 20 µg/mL IαI. Control cells were seeded in Gelatin-coated (0.1%) wells in 2i medium as shown in FIG. 4. The cells were also allowed to grow for 24-48 hours and pictures were taken of the attached cells and the floating spheres in the supernatant. None of the conventional coatings promoted attachment of the E14 mES cells grown in 2i media i.e. Gelatin, fibronectin and collagen all failed as suitable coating proteins for the 2i media formulation for the mES cell line E14. Only vitronectin supported attachment and growth of the mES colonies. When adding 2% FBS as a coating solution or as a supplement to the 2i media almost all the cells attached to the cell culture plastic. When coating the plastic with IαI or the cleaved globular part HC2 the cells also attached in the 2i media. When adding the human purified IαI protein as a supplement to the 2i media the cells also attached to the cell culture media as shown in FIG. 4.

Example 3

Long-Term Culture of E14 mES Cells in 2i Media for 20 Passages

The E14 mES cell line grown in 2i media was passaged in serum-free conditions using TryPLE™ and then plated in 2i media, 2i media 2% FBS or 2i media with 10 µg/mL of IαI. The cells in the supplemented medias attached to the cell culture plastic while the control cells (2i media alone) continued to grow as floating spheres. The cells grown in 2i media with 2% FBS showed a high attachment ratio with an increased spreading of the cells on the plate. However, under these conditions some colonies lost the tight colony morphology typical for mES cell colonies. The cells grown in the IαI-supplemented media also attached to the plastic, but did not lose the tight colony morphology. The cultures were maintained for 20 consecutive passages with maintained self-renewal and very low levels of differentiation. To investigate whether the cells retained their pluripotency, they were let to form embryoid bodies in hanging drops (1600 cells/drop) for 4 days and then allowed to adhere to cell culture plastic and subsequently differentiate for 6 days. No difference in the amount of EB-outgrowths containing beating cardiomyocytes was seen between the different media formulations.

Example 4

Attachment of Human PS Cell Lines in E8 Media on Different Coated/Supplemented Conditions with IαI and HC2

Figure 5:
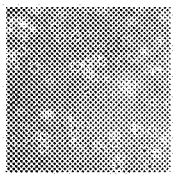
FIG. 5 shows attachment assay bright-field images of human iPS cell line K02C in E8 media on: non-coated plastic, plastic coated with a vitronectin peptide (Vitronectin XF™, StemCell Technologies) for 1 h at RT, non-coated plastic with a supplementation in the media of 10 μg/mL of IαI, and on plastic coated with 20 μg/mL of IαI-HC2 ON at 4° C.
Figure 5:
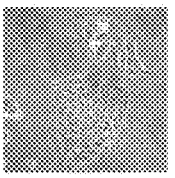
Figure 5:
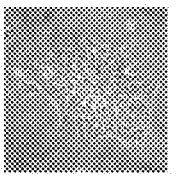
Figure 5:
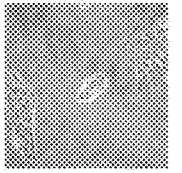

The human induced pluripotent stem cells line K02C and the human ES cell lines H181, H207 (kindly provided by Dr. Outi Houvatta) and HUES1 (kindly provided by Dr. Douglas A. Melton) were routinely cultured on Matrigel® (BD Biosciences, hES-qualified matrix) and the mTERS1® (StemCell Technologies, defined media containing BSA). Stepwise media adaptation was used to adapt culture from mTeSR™ to TeSR™-E8™ media and the adapted cultures were seeded onto Vitronectin-FX™ coating and TeSR™-E8™ media (StemCell Technologies) before the experiment. Human PS cells grown in E8 media were treated with ROCKi Y27632 (StemCell Technologies) and passaged using a gentle dissociation solution (0.5 M EDTA pH 8.0) and a cell lifter to collect small size colonies, additional mechanical breakup of the colonies was done pipetting with a P1000. The colonies were seeded on a 12 well plate with: non-coated surface, Vitronectin-coated surface (1 h at RT), IαI-HC2 coated surface (20 µg/mL in PBS ON at 4° C.) and on non-coated surfaces with 10 µg/mL IαI supplementation of E8 media added in the well. After 24 hours the media in the wells was changed and pictures were taken to assess cell attachment. The human PS cells did not attach to the non-coated surface. The positive control with vitronectin coating achieved normal levels of human PS cell attachment. The addition of IαI to the E8 media stimulated the attachment of the human PS cells to a similar extend as vitronectin coating. The IαI-HC2 coated wells achieved lower but still remarkable attachment of cells as compared to the vitronectin coating or the IαI supplemented media as shown in FIG. 5.

Example 5

Figure 7:
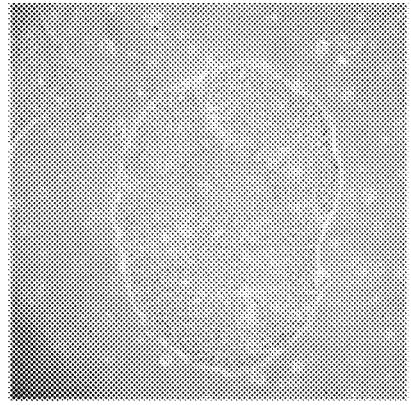
FIG. 7 shows bright-field microscope images of the human PS cell line K02C adapted to growing in the minimal E8 media in two different conditions: Vitronectin coating (Vitronectin FX™, Stem Cell Technologies) for 16 passages, and on non-coated plastic supplemented with 20 μg/mL IαI for 14 passages.
Figure 7:
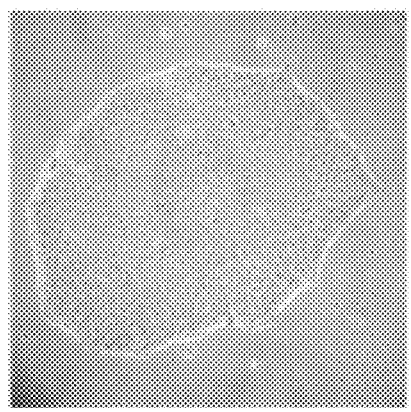

Long-Term Culture of Human PS Cells in TeSR™-E8™ Media Supplemented with IαI on Non-Coated Plastic The human induced pluripotent stem cells line K02C and the human ES cell lines H181, H207 (kindly provided by Dr. Outi Houvatta) and HUES1 (kindly provided by Dr. Douglas A. Melton) were routinely cultured on Matrigel® (BD Biosciences, hES-qualified matrix) and the mTERS1® (StemCell Technologies, defined media containing BSA). Stepwise media adaptation was used to adapt culture from mTeSR™ to TeSR™-E8™ media and the adapted cultures were seeded onto Vitronectin-FX™ coating and TeSR™-E8™ media (StemCell Technologies). After one passage of adaptation of the human PS cells to TeSR™-E8™ and Vitronectin-FX™, the human PS cells were passaged using a gentle dissociation solution (0.5 M EDTA pH 8.0) and a cell lifter (TPP) to collect small size colonies. Part of the cells were then seeded onto non-coated plastic with TeSR™-E8™ supplemented with 20 µg/mL of purified IαI complete human protein. All four human PS cell lines showed attachment when seeded onto non-coated plastic with media supplemented with IαI. Cultures using both IαI supplementation or Vitronectin-FX™ coating were kept for long-term culture. The novel media formulation of TeSR™-E8™ supplemented with 20 µg/mL IαI maintained the human PS cells for over 20 passages in a similar manner as the commercial formulation of TeSR™-E8™ combined with Vitronectin-FX™ coating. FIG. 7 shows how the colonies keep the same morphology after 14 passages using IαI supplementation.

Example 6

Immunocytochemistry of Pluripotency Markers

The human PS cell lines adapted to grow on TeSR™-E8™ on Vitronectin-FX™ coating or 20 µg/mL IαI supplementation and the mouse ES cells adapted to grow on 2i media supplemented with 2% FBS or 10 µg/mL IαI were checked for pluripotency markers using immunocytochemistry and Alkaline phosphatase staining. Oct3/4, Nanog, Sox2 were checked on mouse ES cells using immunocytochemistry. Both culture conditions show high levels of pluripotency markers with negligible or no signs of differentiation. The human PS cell lines K02C and H181 were checked using immunocytochemistry for the extracellular pluripotency markers Tra-1-60, Tra-1-80 and SSEA-4 alone or in combination with antibodies against IαI-HC1 and HC2. Both culture conditions maintained pluripotency marker expression on both cell lines. Moreover, IαI-HC2 showed a pattern similar to the pluripotency markers, being only positive on colonies also positive for pluripotency markers and not staining colonies that had started differentiation. In conclusion, addition of IαI to the media maintains pluripotency on serum free cultures on both mouse and human PS cells after 5 passages.

Alkaline-Phosphatase Staining

Figure 8:
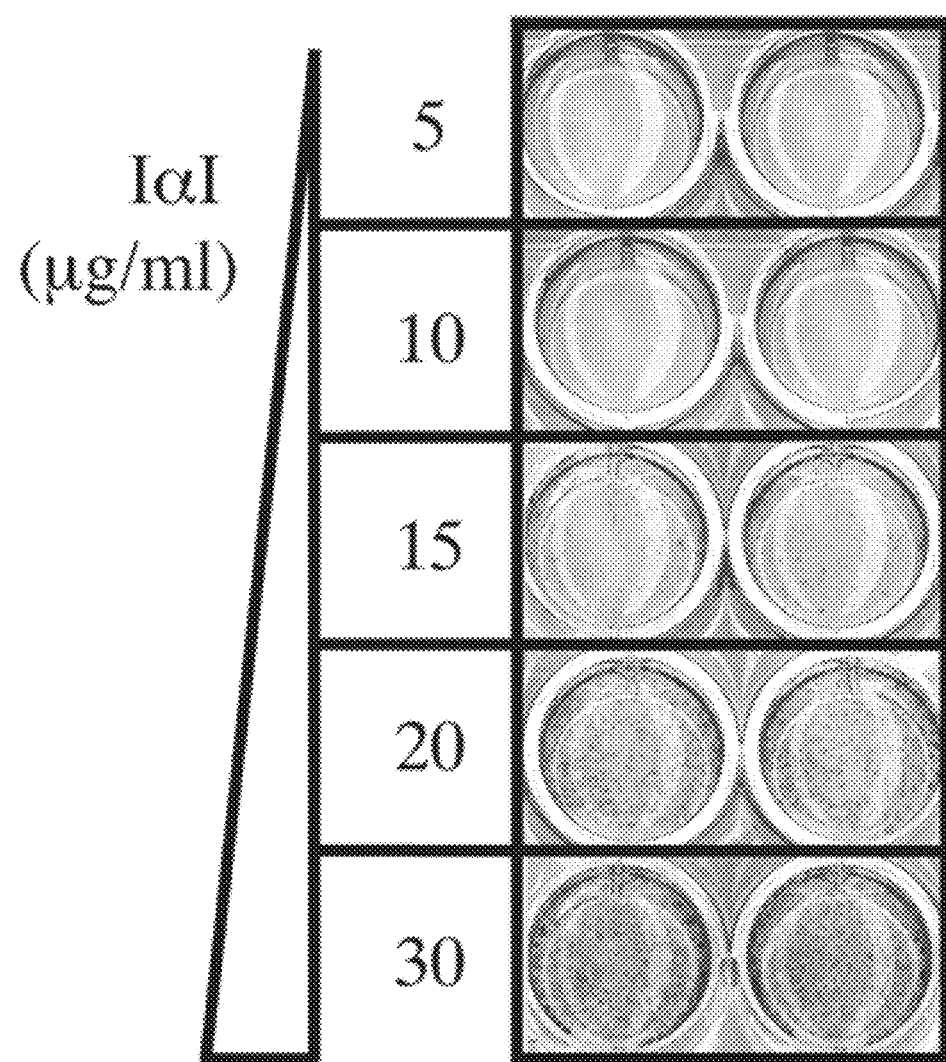
FIG. 8 shows alkaline phosphatase positive K02C hiPS cell colonies attached onto non-coated plastic wells using increasing concentrations of IαI in TeSR™-E8™ media three days after seeding.

The human PS cell lines H181 and K02C adapted to grow on TeSR™-E8™ and Vitronectin-FX™ coating were seeded using 0.5 EDTA pH 8.0 and a cell lifter and small colonies were seeded on a 12 well plate using TeSR™-E8™ media supplemented with different concentrations of human purified IαI complete protein. After two or three days of growing the cells were stained using an Alkaline Phosphatase kit (Life Technologies) in order to visually detect the pluripotent human PS colonies. Higher concentration of IαI achieved higher attachment and growth rates of the human ES cells as shown in FIG. 8.

Example 7

Single Cell Splitting with or without ROCKi

When sub-culturing in small aggregates, 50 µg mL$^{-1}$ of IαI supplementation at the seeding step support similar viability as VN-FX coating. However, when performing single-cell splitting, almost no cells had survived after 4 days on VN-FX coating even with the addition of 10 µM ROCKi to the culture during the first 24 hours after seeding. In contrast, under these conditions, IαI supplementation supported very high cell survival, with cells reaching a monolayer after 4 days. Further analysis showed that IαI was also able to support survival and colony formation of dissociated single cells in the absence of ROCKi, although the survival rate was lower than with ROCKi. As shown in FIGS. 9 and 10, IαI increases survival after single cell splitting. FIG. 9 shows the quantification of HUES1 and K2C cell survival and growth, using crystal violet staining, after 4 days in culture on VN-FX coat or with IαI supplementation after single-cell passaging with or without addition of 10 µM ROCKi after seeding, no ROCKi pre-treatment. FIG. 10 shows representative images for HUES1 cell line, bright-field pictures on the top and overview of crystal violet on the bottom. All cell number quantification experiments were performed in triplicate over three separate experiments. Bars show mean±SEM in comparison to E8:IαI values.

Example 8

Assessment of Six Different hPS Cell Lines (K2C, HUES1, H207, H181, NCL1 and K8F) Cultured in E8:IαI or E8:VN The cloning success rate for 6 different hPS cell lines (K2C, HUES1, H207, H181, NCL1 and K8F) cultured in E8:IαI or E8:VN has been assessed. High cloning rates of up to 18% were achieved with E8:IαI, and the cloning efficiency was consistently higher using the E8:IαI protocol as compared to E8:VN protocol in all 5 hPS cell lines tested, despite using a 5 hour pre-treatment with ROCKi as shown in Table 1. Specifically, cloning efficiency of individualized HUES1, K2C, H207, H181, K8F and NCL1 hPS cells were assessed in 96-well plates using E8:IαI (E8 medium with 50 µg mL$^{-1}$ IαI supplementation) or E8:VN (E8 medium on vitronectin-coated surface) with 5-hour pre-treatment and supplementation of 10 µM ROCKi for the first 48 h. Assessment of colonies was done 14 days after seeding through MTT-assay.

TABLE 1

IαI increases clonal efficiency of hPS cells.

| hPS line | Culture Method | Number of wells | Wells with 1 colony | Cloning efficiency (%) |
|---|---|---|---|---|
| HUES1 | E8:VN | 298 | 7 | 2.3 |
| HUES1 | E8:IαI | 451 | 50 | 11.1 |
| K2C | E8:VN | 100 | 0 | 0 |
| K2C | E8:IαI | 200 | 10 | 5 |
| H207 | E8:VN | 100 | 1 | 1 |
| H207 | E8:IαI | 93 | 7 | 7.5 |
| H181 | E8:VN | 200 | 2 | 1 |
| H181 | E8:IαI | 200 | 14 | 7 |
| K8F | E8:VN | 300 | 29 | 9.7 |
| K8F | E8:IαI | 284 | 32 | 11.3 |
| NCL1 | E8:IαI | 275 | 50 | 18.2 |

Example 9

IαI and its HC2 Domain Induce hES Cell Attachment

To study whether IαI could support stem cell attachment, K2C hiPS cells were seeded onto standard tissue-culture (TC) treated plastic in E8 medium supplemented with 50 µg ml$^{-1}$ IαI. The purity of the isolated IαI protein solution was thoroughly validated through silver staining and mass spectrometry analysis. Cell attachment was assessed 4 hours after seeding using crystal violet staining, and VN-FX coated plates (E8:VN) were used as positive control. The result shows how IαI supplementation induces similar cell attachment levels as VN-FX coating. The separate Bk, HC1 and HC2 domains were all unable to support attachment when added in solution to the medium. However, when HC2 (but not HC1) was pre-coated onto standard TC-treated plastic, similar attachment levels as with IαI supplementation were achieved 4 hours after seeding. Cells seeded in IαI or on HC2 coated plates exhibited similar colony morphology and cell-cell contacts (defined by E-cadherin arrangement) as cells seeded on VN-FX. To further investigate the role of the different IαI-domains in the hPS cell attachment we added antibodies against each of the three IαI domains at the seeding step. Even though the use of the separate IαI domains showed HC2 to be responsible for the hPS cell attachment, all three antibodies inhibited IαI-induced attachment regardless of which domain was being targeted, suggesting that antibody binding hinders IαI-mediated attachment when used in solution.

Example 10

IαI Efficiently Supports Single-Cell Passaging of hPS Cells

To further evaluate IαI-induced hPS cells attachment and growth; HUES1 and K2C hPS cells were dissociated into small aggregates using a gentle enzyme-free reagent (Gentle Cell Dissociation Reagent (GCDR, Stem Cell Technologies)), or into single cells using TrypLE (a recombinant cell-dissociation enzyme, ThermoFisher) with ROCKi supplementation. The cells were then seeded using E8:VN or E8 with different IαI concentrations ranging from 0-500 μg ml$^{-1}$. On day 4, cell density was assessed using crystal violet staining. The results obtained shows that 40-100 μg ml$^{-1}$ of IαI was able to support attachment, characteristic colony morphology and positive alkaline phosphatase staining; 50 μg ml$^{-1}$ IαI was therefore selected for all subsequent experiments (and is denoted as E8:IαI). It was also confirmed that IαI-addition is only required during seeding and the initial attachment process, and is not required in subsequent medium exchanges.

When sub-culturing in small aggregates, 50 μg ml$^{-1}$ of IαI supplementation at the seeding step supported similar viability as VN-FX coating. However, when performing single-cell splitting, almost no cells had survived after 4 days on VN-FX coating even with the addition of 10 μM ROCKi to the culture during the first 24 hours after seeding. In contrast, under these conditions, IαI supplementation supported very high cell survival, with cells reaching a monolayer after 4 days. Further analysis showed that IαI was also able to support survival and colony formation of dissociated single cells in the absence of ROCKi, although the survival rate was lower than with ROCKi (FIG. 9 and FIG. 10). Live monitoring of hES cells (HUES1) cultured in the absence of ROCKi showed that although the cells initially attach and spread as single cells on VN-FX coating, they eventually lift off the plate and die, while HUES1 cells seeded in the presence of IαI exhibit decreased motility after seeding but stronger cell-to-cell contact formation, and grow as adherent colonies until they are ready to be passaged.

As presented above, in the absence of ROCKi pre-treatment, no hPS cell survival was observed on VN-FX coating. A one-hour pre-treatment with ROCKi is usually recommended for single-cell splitting of hPS cells to increase cell survival. However, in our hands, one-hour pre-treatment resulted in inconclusive results when using the E8:VN method, even at high seeding densities. To prevent this, the ROCKi pre-treatment step was increased to 5 hours. This longer pre-treatment improved the survival in E8:VN, but not to the level seen with E8:IαI. There was a consistent higher cell density after 4 days in E8:IαI cultures when compared to VN-FX coating, from very low cell-seeding densities (25 cells cm$^{-2}$) up to typical seeding densities (10$^3$ cells cm$^{-2}$).

Example 11

Easy Adaptation of hPS Cell Lines to E8: IαI

To ensure that the E8:IαI protocol can support robust propagation and pluripotency of different hPS cells, six hES cell lines (HUES1, H181, H207, OXF2, NCL1, huES3-Hb9::GFP) and two hiPS cell lines (K2C and K8F), originally derived in four different laboratories, were adapted to E8:IαI. All hPS cell lines exhibited normal morphology in E8:IαI medium. The E8:IαI protocol showed better adaptation efficiency of the hES cell line OXF2 from feeder-cell culture as compared to E8:VN. Through a simple step-wise adaptation protocol, combining E8:IαI and single-cell passaging using TrypLE dissociation and ROCKi, we achieved 100% adaptation efficiency of 5 different feeder-dependent hPS cell lines (OXF2, NCL1, huES3::Hb9rGFP, K2C and K8F), with approximately four fold better yield as compared to the E8:VN protocol for OXF2 hES cells. Healthy colony formation was achieved at passage 1 and negligible differentiation was observed from passage 2. Successful adaptation of NCL1 was particularly noteworthy since this line had, in our hands, proved incompatible with feeder-free culture. These data suggest enhanced adaptation efficiency of feeder-dependent hPS cell lines to E8:IαI. Assessment after 5-10 passages proved expected stem cell marker expression.

Example 12

IαI Supports Long-Term Propagation of hPS Cells

Three hES cell lines (HUES1, H207 and H181) and one hiPS cell line (K2C) were then cultured for 15 or more passages in E8:IαI. The E8:VN protocol was used as positive control and, for adequate comparison, cells were split in small clumps for both protocols. All cell lines grew as tight colonies with negligible signs of differentiation regardless of culture condition. E8:IαI also supported freeze-thaw cycles with survival rates after recovery similar to E8:VN. Proliferation rate was assessed for up to 40 days (10 passages) and showed similar growth rates independent of culture protocol and cell line. Immunofluorescence staining highlighted strong and specific expression of stem cell markers in all cell lines after 15 or more passages in both protocols.

The Human Stem Cell Pluripotency TaqMan array (ThermoFisher) was performed to characterize expression profiles of the four hPS cell lines after long-term propagation focusing on marker genes for pluripotency, sternness and differentiation. No significant differences in transcription profiles were found between culture conditions (as determined by multiple comparisons using two-way ANOVA and Sidak's Multiple test), indicating that II does not induce differentiation or reduce expression of stem cell related markers. Indeed, when relative expression values for stem cell markers were assessed closely, it was found that hPS cells grown in E8:IαI showed a more compact expression profile than hPS cells grown in E8:VN. The cells were then subjected to spontaneous differentiation by embryoid body formation and subsequent plating onto Matrigel™ with serum-containing medium. After four weeks, all hPS cell lines, independent of previous culture condition, showed successful differentiation into the three germ layers as assessed by immunofluorescence staining for specific markers. TaqMan array was then performed on the differentiated hPS cell samples and again, no differences in transcriptional profiles were found between the two culture methods. Moreover, as shown in Supplementary Movie 4, K2C hiPS cells successfully produced beating cardiomyocytes after 40 passages in E8:IαI.

Example 13

IαI Supports Directed Endoderm Differentiation

Endoderm has been the most difficult germ layer to generate in vitro. In order to investigate if II could also support directed differentiation protocols for hPS cells, we combined the STEMDiff™ Definitive Endoderm Kit (TeSR-E8 optimized, StemCell Technologies) with IαI. Briefly, four hPS cell lines grown in E8:IαI for 10 or more passages were pre-conditioned to endoderm before being split as single-cells and seeded using IαI. All four hPS cell lines attached normally and survived throughout the five-day differentiation protocol. The results showed that cells cultured in E8:IαI can be readily induced to differentiate into endoderm, generating a mono-layer of endoderm precursor cells, positive for the key early endoderm markers Sox7, Sox17 and HNF-3β.

Example 14

IαI does not Increase Genetic Abnormalities

In order to ensure that IαI does not increase the level of mutations or chromosomal abnormalities after long-term culture when compared to current methods, all hPS cell lines were subjected to G-banding and the Human OmniExpressExome array (Illumina, SNP&SEQ Technology Platform, Uppsala University). Single nucleotide polymorphism (SNP)-array data were analyzed both by total number of copy number (CN)-calls, and number of shared CN-calls between early and later passage. G-banding analysis showed few but equal amounts of abnormalities in both culture methods. Further analysis done by using SNP-array data indicates that the CN-profiles changed during culturing regardless of protocol used and cell-line examined and that the two examined protocols perform equally well in retaining genetic profiles. A stricter CN-analysis was also performed by comparing the number of shared CN-calls between early and late passages in each of the four cell-lines under the two protocols and for all 123 CN-calls. Overall, we found no difference in the number of genetic alterations detected (Wilcoxon rank-sum-test; W=10.5, p=0.8082). No increase in genetic abnormalities was observed in E8:IαI as compared to E8:VN and the starting passages, suggesting that IαI does not increase the risk of genetic aberrations or selection for advantageous mutations in long-term culture. Even though the presence of abnormalities in all conditions may seem alarming, the hPS cell lines used in this study were obtained at high passages, and it has been reported that hPS cell lines can develop abnormalities after long-term culture in vitro. Indeed, a previous large-scale analysis of 125 independent hPS cell lines from 38 different laboratories reported that small variations similar to the ones present in this study could be found in all samples, and documented that these are consistent with previous structural variants studies made on human populations, therefore dependent on their source genome and not from their in vitro culture.

The embodiments above are intended to be illustrative and not limiting. Additional embodiments are within the claims. In addition, although the present disclosure has been described with reference to particular embodiments, those skilled in the art will recognize that changes can be made in form and detail without departing from the spirit and scope of the disclosure. Any incorporation by reference of documents above is limited such that no subject matter is incorporated that is contrary to the explicit disclosure herein.

What is claimed:

1. A method for culturing stem or progenitor cells, the method comprising providing a cell-free medium comprising 2 g/mL-100 g/mL of one or more proteins selected from the group consisting of an IαI protein comprising heavy chain 1 (HC1), heavy chain 2 (HC2), and bikunin (B) IαI-HC1, HC2, B), an isolated HC2, and any other IαI protein comprising heavy chain 2 (IαI-HC2) seeding the medium with the cells on an uncoated culture surface and optionally allowing the cells to grow in the medium
    wherein the one or more IαI proteins promote adhesion of said cells to said uncoated surface, and
    wherein the medium is partially or completely chemically-defined, and wherein the medium is whole serum-free, serum component-free and feeder cell-free.

2. The method of claim 1, wherein the one or more IαI proteins are un-complexed proteins isolated from serum or a serum fraction, produced as a recombinant protein, synthesized chemically, or a combination thereof.

3. The method of claim 1, wherein said uncoated surface is an uncoated plastic culture surface.

4. The method of claim 1, wherein the stem cells are pluripotent stem (PS) cells.

5. The method of claim 1, wherein the cells are of human origin.

6. The method of claim 1, wherein the completely chemically defined medium is E8.

7. The method of claim 1, wherein the partially chemically defined is 2i medium.

8. The method of claim 1, wherein the concentration of the one or more IαI proteins in the medium is 10 g/mL-50 g/mL.

9. The method of claim 1, wherein the one or more IαI proteins comprise the IαI-HC1, HC2, B protein.

10. The method of claim 1, wherein the one or more IαI proteins comprise the isolated HC2.

11. The method of claim 1, further comprising growing the stem or progenitor cells for at least five passages in said medium.

12. A method of using one or more isolated IαI proteins for cell adhesion and self-renewal of PS cells on an uncoated cell culture surface, the method comprising, contacting cell-free medium with 2 g/mL-100 g/mL of the one or more isolated IαI proteins and with the cells wherein the one or more isolated IαI proteins promote the adhesion of said cells to the uncoated surface wherein the one or more IαI proteins are selected from the group consisting of IαI-HC1, HC2, B protein, an isolated HC2, and an IαI-HC2,
    wherein the medium is partially or completely chemically defined, and wherein the medium is whole serum-free, serum component-free and feeder cell-free.

13. The method of claim 12, wherein the PS cells are primed or naive embryonic stem (ES) cells or induced pluripotent stem (iPS) cells.

14. The method of claim 12, wherein the one or more IαI proteins comprise the isolated HC2.

15. The method of claim 12, further comprising adding Rho-associated kinase inhibitor (ROCKi) to the cell culture medium to support single cell survival.

16. The method of claim 12, further comprising growing the cells to a colony.

17. The method of claim 12, wherein the cells are of human origin.

18. The method of claim 12, wherein the concentration of the one or more IαI proteins is 10 g/mL-50 g/mL in the cell culture medium.

19. A method for culturing stem or progenitor cells, the method comprising growing said cells during the first passage on an uncoated plastic surface in a cell-free cell-culture medium wherein the medium has been supplemented with isolated IαI proteins selected from an isolated IαI-HC1, HC2, B and an isolated HC2, to promote adhesion of said cells to said uncoated surface as well as self-renewal of said cells, wherein the cell culture medium is partially or completely chemically defined, whole serum free, serum component free, and feeder cell free, wherein the one or more IαI proteins are isolated from serum or a serum fraction, produced as a recombinant protein, synthesized chemically, or a combination thereof.

20. The method of claim 19, wherein the cell culture medium is E8.

21. The method of claim 19, wherein the concentration of the one or more IαI proteins is 0.1 g/mL-200 g/mL in the cell culture medium.

22. The method of claim 19, further comprising growing the cells to a colony.

23. The method of claim 19, wherein the stem cells are PS cells.

24. The method of claim 19, wherein the cells are of human origin.

25. The method of claim 19, further comprising culturing the stem or progenitor cells for at least five passages in said cell culture medium to produce undifferentiated or unmutated cells.

26. The method of claim 19, further comprising growing the stem or progenitor cells for at least twenty passages in said cell culture.

27. The method of claim 19, further comprising optionally adding ROCKi to the cell culture medium to support single cell survival.

28. The method of claim 19, wherein the cell culture medium is 2i.

* * * * *